United States Patent [19]
Black et al.

[11] Patent Number: 5,667,386
[45] Date of Patent: Sep. 16, 1997

[54] APPARATUS, SYSTEM, AND METHOD FOR READAPTING A DENTAL APPLIANCE

[75] Inventors: Sheldon L. Black; John H. Bailey; Dan E. Fischer, all of Sandy, Utah

[73] Assignee: Ultradent Products, Inc., South Jordan, Utah

[21] Appl. No.: 483,336

[22] Filed: Jun. 7, 1995

[51] Int. Cl.$^6$ .................................................. A61C 11/00
[52] U.S. Cl. .......................................... 433/213; 425/504
[58] Field of Search ...................... 433/6, 213; 425/504; 269/21

[56] References Cited

U.S. PATENT DOCUMENTS

| | | | |
|---|---|---|---|
| 3,398,434 | 8/1968 | Alesi, Jr. et al. | 425/504 |
| 3,600,752 | 8/1971 | Kopp | 425/504 X |
| 4,028,042 | 6/1977 | Goodfellow et al. | 425/504 |
| 5,437,828 | 8/1995 | Shimizu et al. | 425/504 X |

*Primary Examiner*—Nicholas D. Lucchesi
*Attorney, Agent, or Firm*—Workman Nydegger Seeley

[57] ABSTRACT

An apparatus, system, and method for readapting a dental appliance to better fit a model of a wearer's teeth using a vacuum forming table and a heating element is disclosed. The readaptation apparatus is provided with an elastic membrane for closely conforming the dental appliance to the contours of the model upon application of negative pressure to the model and with a drum head adapter for retaining the elastic membrane to the surface of the vacuum forming table in order to efficiently readapt the dental appliance. The disclosed system includes the described readaptation apparatus, as well as a specialized vacuum forming device. The vacuum forming device positions the dental appliance a specific distance from a heating element on the vacuum forming device for bringing the dental appliance to a proper state of plasticity and then smoothly relocates it to the surface of the vacuum forming table, where the dental appliance is vacuum formed using the readaptation apparatus. The inventive method comprises forming the dental appliance using the vacuum forming device, trimming the dental appliance, and then readapting the dental appliance to better fit the model. This is done by heating it to a proper state of plasticity at a predetermined position on the vacuum forming device with an inventive positioning mechanism, relocating the appliance smoothly onto the vacuum forming table, and then vacuum forming the dental appliance to fit the model using the readaptation apparatus to sustain a negative pressure around the model and dental appliance.

45 Claims, 9 Drawing Sheets

APPARATUS, SYSTEM, AND METHOD FOR READAPTING A DENTAL APPLIANCE

BACKGROUND OF THE INVENTION

1. The Field of the Invention

The present invention relates to apparatus, systems, and methods for forming dental appliances. More specifically, the present invention is directed to an apparatus, system, and method for readapting a dental appliance to closely conform the shape of the dental tray to the teeth of a patient with the use of a vacuum forming device.

2. The Relevant Technology

Dental appliances are frequently used in dentistry for such applications as bleaching, fluoridizing, treatments of caries diseases, mouth guards, night guards, bite adjustor trays, and registration bases. It is necessary that dental appliances be well fitted to closely conform to the teeth of the patients on which they are to be worn. Improperly fitting dental appliances tend to irritate the gums, are difficult to retain on the teeth and gums, and may allow treatment substances contained within them to leak out into the mouth of the wearer.

The dental field currently uses a procedure of forming dental appliances and of adapting them to fit the teeth on which they are to be worn that involves the use of a vacuum forming device. Under this procedure, the dental appliances are formed from a sheet of thermoplastic material by creating a model of the teeth, heating the thermoplastic sheet, and vacuum forming the thermoplastic sheet to the model. Once formed, the dental appliance is removed from the model and the excess plastic is trimmed away. The initial removal from the model and subsequent trimming cause distortion of the dental appliance. In order to remedy the distortion, a second procedure, known as readaptation, is commonly performed. As will be seen, certain inherent difficulties make current readaptation procedures unsatisfactory.

In order to better understand the present invention, the presently known manner of forming a dental appliance to fit a person's teeth with the use of a vacuum forming device will now be described. A representative vacuum forming device is shown in FIGS. 1 and 2, and is available from Ultradent Products, Inc., South Jordan, Utah. The depicted vacuum forming device 10 comprises a body section 12 having located therein a vacuum pump 14 for providing a negative pressure. A vacuum forming table 26 is formed on the body section 12 over the vacuum pump 14. The vacuum forming table 26 is provided with holes 44 leading to the vacuum pump 14 and linked in negative pressure communication therewith. A glide rail 18 extends upward from the body section 12, and a hood 20 containing a heating element 22 is located at the top of the glide rail 18. A two-piece clamping frame 24 is slidably attached to the glide rail 18, such that objects held in the clamping frame 24 may be moved into proximity with the heating element 22, and thereafter quickly relocated to the vacuum forming table 26. The clamping frame 24 is attached to one end of a guide rod 28, and the other end of the guide rod 28 is inserted into a sleeve 30 formed in the body section 12. Adjacent to the sleeve 30 is a perpendicular recess 32 containing a spring-loaded ball mechanism 34. The spring-loaded ball 34 presses against the guide rod 28, and when the clamping frame is raised to a given position close to the heating element, inserts itself into an indentation 36 on the surface of the guide rod 28. Once inserted into the indentation 36, the spring-loaded ball mechanism temporarily maintains the guide rod 28 and the clamping frame 24 in the given position. The application of a sufficient downward force on the clamping frame 24 by the operator overcomes the engagement of the spring-loaded ball with the indentation 36, releasing the clamping frame 24 to move freely.

The clamping frame 24 comprises an upper frame 38 and a lower frame 40 connected with hinges 54. A pair of clamps 52 located at either side of the clamping frame 24 are for clamping the upper frame 38 and the lower frame 40 together, such that a square thermoplastic sheet 42 can be retained within the clamping frame 24. The thermoplastic sheet 42 is typically about four inches in dimension on each side, and is made of material such as polypropylene. The clamps 52 of the depicted device comprise S-clamps, and are capable of generating a constant clamping pressure for sheets of varying thicknesses. An indicator light 46 indicates when the heating element 22 is activated, and an on/off switch 48 activates the heating element 22 and the vacuum pump 14. When the on/off switch 48 is activated, sensors on the device detect the position of the clamping frame. The heating element 22 is enabled when the clamping frame 24 is moved to the given position close to the heating element, and the vacuum pump 14 is enabled when the clamping frame 24 is relocated to rest on the vacuum forming table 26.

The method known in the art of vacuum forming a dental appliance using the described vacuum forming device 10 comprises creating a model 50 in the shape of a set of teeth or gums on which the appliance is to be worn, and then placing the model 50 on the vacuum forming table 26. The thermoplastic sheet 42 is then retained within the clamping frame 24, and the S-shaped clamps 52 of the clamping frame 24 are engaged to clamp the thermoplastic sheet 42 in place. The clamping frame 24 is then positioned close to the heating element 22, as shown in FIG. 1. The spring-loaded ball 34 inserts itself into the indentation 36 in the guide rod 28, with a force sufficient to temporarily maintain the clamping frame 24 in the proper vertical position.

The heating element 22 is then activated by pressing on/off switch 48. Once the thermoplastic sheet 42 is sufficiently heated, it will sag below the clamping frame 24 as shown. When the thermoplastic sheet 42 sags to a proper level, typically where the center of the thermoplastic sheet 42 is about two inches below the level of the frame, the thermoplastic sheet 42 is sufficiently thin and pliable to be formed to the model 50. The clamping frame 24 is then pulled down to rest on top of the vacuum forming table 26, as shown in FIG. 2, and the vacuum pump 24 is automatically activated. Negative pressure from the vacuum pump 14 draws the thermoplastic sheet 42 tightly over the model 50, causing the thermoplastic sheet 42 to closely conform to the model 50 as it cools.

After a sufficient amount of time has passed for the thermoplastic sheet 42 to form to the model 50 and cool sufficiently to retain its shape, the vacuum pump 14 is switched off, and the model 50 and the newly formed dental appliance 54 are removed. The outer portion of the excess plastic around the dental appliance 54 is then trimmed from the dental appliance with a set of utility vinyl cutters 56, as shown in FIG. 3. The dental appliance is then separated from the model 50, and the remaining excess plastic is trimmed away with scalloping scissors 57, as shown in FIG. 4. When finished, the dental appliance 54 properly covers only the teeth, with the portions extending above or below the teeth having been removed. As a final step, a flame torch 58 is used to polish and smooth the edges of the dental appliance 54, as shown in FIG. 5.

As mentioned, the initial removal of the dental appliance from the model causes distortion of the dental appliance.

Trimming the dental appliance to fit the teeth also causes distortion. A distorted appliance 54 is shown in FIG. 5. Distorted dental appliances tend to fit less tightly around the base of the teeth. Edges protrude and irritate the gums, and the dental appliance loosens at the base of the teeth. Consequently, any treatment materials carried within the dental appliance, such as bleaches or fluorides will tend to leak from the dental appliance into the mouth of the wearer. The resulting disadvantages can be readily appreciated. For instance, the treatment materials are often foul tasting, may irritate the gums of the wearer, or may cause other undesired effects. Furthermore, such leakage is inefficient and wasteful, driving up the cost of dental procedures. To remedy this problem, readaptation methods are commonly used in order to provide the dental appliances with a better fit to the mouth of the wearer.

3. Prior State of the Art

In the past, readaptation has been accomplished with the use of a flame torch. The flame torch typically comprises the small, hand-held, gas-powered torch 58 of FIG. 5. Since the thermoplastic materials used in forming dental appliances are too soft for rotary polishing, one function of the flame torch 58 has typically been to polish the dental appliances and smooth its edges, as previously mentioned. Readaptation has also been accomplished with the use of the flame torch 58 using a procedure of heating the dental appliance 54 on the model 50, as shown in FIG. 5, and then manually forming the dental appliance 54 into place as it cools. The forming of the dental appliance into place is typically accomplished by dipping a finger into a reservoir of water and then pressing the finger to the dental appliance 54, holding the dental appliance in place on the model 50 as the model 50 is cooled by the water. This process of heating and pressing on the dental appliance 54 is repeatedly carried out until the dental appliance 54 conforms more closely to the model 50. As is apparent, a major disadvantage to this process is that it is very time consuming. Furthermore, it is difficult, if not impossible, using this process, to cause the dental appliance 54 to conform precisely to the model 50, and thus to the teeth of the wearer. A readapted dental appliance 54 is shown in FIG. 6.

Other dental procedures are known to have used vacuum forming to create and fit related devices. For instance, a procedure was used in the early seventies by students at the Loma Linda Dental College in California to form registration bases for dentures. The procedure comprised the use of a vacuum device fixed to a cabinet. The registration bases were formed on an X-shaped opening located over the vacuum device. A cylinder with a rubber dam tightly fastened to the cylinder was used as a method of conforming the registration bases to casts of the wearer's gums. The registration bases were formed from a resin based material called shellac that achieves plasticity with low amounts of heat. In the procedure, the shellac material was heated with a heat lamp and placed over the cast of the gums, and the rubber dam, tautly stretched on the cylinder, was placed over the shellac material. The rubber dam was drawn by negative pressure down over the registration base, conforming the shellac material to the cast as the registration base cooled.

While this procedure worked sufficiently for the desired purpose, it was never contemplated for the use of forming dental appliances to fit models of teeth. As then known, the tightly stretched rubber dam worked sufficiently on models of gums, but it was used only with highly plastic materials that are very malleable with low amounts of heat, was used only with casts of gums, and would be inadequate for use with the thermoplastic materials used today. Such modern thermoplastics require more heat in specific amounts, and are not as malleable as the Shellac material. Furthermore, models of teeth have deep embrasures between the representations of teeth, and greater contours than models of gums. The tight fitting rubber dam of this method would not be able to conform to those embrasures and contours, especially using modern thermoplastics, and thus could not produce a dental appliance that properly fits a set of teeth. Part of the present invention, as will later be seen, is the discovery that this process could be modified for the readaptation of dental appliances.

From the above discussion, it can be seen that a need exists in the art for a method to accompany current adaptation procedures, whereby a dental appliance can be readapted in a manner that is less time consuming than currently known procedures. Such a method is also needed that will provide the dental appliance that will closely correspond to the teeth, such that the dental appliance will not irritate the gums, will not fall off, and will not leak its contents. It would also be advantageous if such a method could be accomplished by utilizing the same vacuum forming table to effect readaptation as was originally used to form the dental appliance.

SUMMARY AND OBJECTS OF THE INVENTION

The present invention seeks to resolve the above and other problems which have been experienced in the art. More particularly, the present invention constitutes an advancement in the art by providing an apparatus, system, and method for readapting a dental appliance which achieves each of the objects listed below.

It is an object of the present invention to provide an apparatus, system, and method for readapting a dental appliance to provide a better fit of the dental appliance to the teeth of the wearer.

It is likewise an object to provide such an apparatus, system, and method that substantially reduce leakage to provide better control of processes for introducing materials into the mouth of the wearer for prolonged periods of time.

It is also an object of the present invention to provide such an apparatus, system, and method that utilize the same vacuum forming device for readaptation as was originally used for adaptation.

It is another object of the present invention to provide such an apparatus, system and method that allow readaptation to be performed in less time and without manual manipulation of the dental appliance.

It is still a further object of the present invention to provide such an apparatus, system, and method that can be used to readapt dental appliances of types used in a broad variety of applications, such as bleaching trays, fluoridizing trays, mouth guards, night guards, treatment trays, and registration bases.

It is also an object of the present invention to provide such an apparatus, system, and method wherein the cost of services such as bleaching, fluoridizing, and other such services requiring the use of a dental appliance can be provided at a lower cost.

It is also an object of the present invention to provide such an apparatus, system, and method that are safe and easy to use.

To achieve the foregoing objects, and in accordance with the invention as embodied and described herein, the present invention comprises an apparatus, system, and method for readapting a dental appliance such that the dental appliance will conform closely to the teeth from which the model was taken. The apparatus of the present invention comprises means for pressing the dental appliance closely to the contours of the model upon application of negative pressure. In one embodiment, the apparatus of the present invention comprises an elastic membrane and a means for sealing the elastic membrane to the surface of a vacuum forming table. The sealing means in one embodiment comprises a drum head adapter and a fastening means that retains the outer periphery of the elastic membrane to a planar rim surface located on the drum head adapter.

Using the drum head adapter, the elastic membrane is placed over a dental appliance and model that are located on a vacuum forming table. The edges of the elastic membrane are sealably held to the vacuum forming table by the drum head adapter in order to sustain a negative pressure around the model and dental appliance when a vacuum pump in negative pressure communication with the vacuum forming table is enabled. The low tension with which the elastic membrane is fastened to the drum head adapter enables the negative pressure to draw the elastic membrane tightly around the model so as to conform closely to the embrasures and contours of the model, causing a tight fit of the dental appliance to the model when the dental appliance has cooled.

The system of the present invention involves the use of the readaptation apparatus in combination with a vacuum forming device of the type described in the background section above, having a vacuum pump, a vacuum forming table, and a heating element. The vacuum forming device is modified as part of the present invention with means for positioning the model and dental appliance in a predetermined position with respect to the heating element and with means for relocating the model and dental appliance to the vacuum forming table. The relocating means allows the model to first be held in the proper heating position, and then to be smoothly and quickly relocated to a position resting on the vacuum forming table, where a negative pressure can be sustained around it with the readaptation apparatus.

One embodiment of the system of the present invention involves the use of a retaining screen clampably held in a clamping frame movably located on the vacuum forming device, on which the model and dental appliance can be supported. A glide rail, to which the clamping frame is movably attached, allows the model and dental appliance to be smoothly relocated from a first position near the heating element to a second position near the vacuum forming table. A guide rod attached to the clamping frame at one end is engagable at a second end with a spring-loaded ball mechanism. The spring-loaded ball mechanism temporarily maintains the clamping frame in the proper vertical position near the heating element. In accordance with the present invention, this position is further away from the heating element than the original adaptation position discussed in the Relevant Technology Section, above.

A method of readapting the dental appliance is also part of the present invention and is used in conjunction with the system and apparatus described above. The method of the present invention involves the following procedure. Initially, the thermoplastic sheet is formed to fit a model at a first position close to a heating element in the manner described above. The formed sheet is then removed from the model, and the excess material is trimmed, transforming it into a dental appliance. The dental appliance is then placed back on the model. The retaining screen is inserted between upper and lower frames of the clamping frame on the vacuum forming device, and clamps are then engaged to hold the retaining screen in place. The dental appliance and model are then placed on the retaining screen, which is elevated to the proper vertical position relative to the heating element for heating the dental appliance to a predetermined level of plasticity.

After the dental appliance has been heated to the proper state of plasticity, the clamping frame is then relocated onto the vacuum forming table. The dental appliance is thereby positioned on the vacuum forming table in close contact with negative pressure from the vacuum pump. The readaptation apparatus described above is then placed over the model and appliance, with the edges of the elastic membrane sealably held to the vacuum forming table. The vacuum pump is then enabled and allowed to run until the negative pressure created around the model and dental appliance causes the dental appliance to conform closely to the model. The appliance is then heated with a flame torch to polish it and smooth its edges, after which it is removed from the model. Polishing and removal of the dental appliance from the model the second time causes little distortion. Consequently, the dental appliance will closely correspond to the model and thus the set of teeth from which the model was taken.

Thus, an apparatus, system, and method for readapting a dental appliance are provided that can be used with models of teeth or gums, that can utilize modern thermoplastics, that are less time consuming than the methods and devices currently known, and that provide the dental appliance with a close fit to the teeth, such that the dental appliance will have a significantly reduced tendency to irritate the gums, fall out of the mouth, or leak its contents. Also, with the use of the present invention, readaptation can be accomplished by utilizing the same vacuum forming table as was originally used to adapt the dental appliance.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained and better understood, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention comprises an apparatus, system, and method for readapting a dental appliance. The present invention is intended for use with a dental appliance that has been previously formed on a model taken from a set of human teeth by a process such as vacuum forming and is intended to provide a more precise fit to the model than that provided by the original adaptation procedure. The present invention also conveniently uses the same vacuum forming table as has been previously used in the art to form dental appliances, with modifications as herein described, in order to quickly, conveniently, and effectively readapt the dental application to achieve a proper fit. Readaptation under the present invention involves heating the dental appliance on the model to a predetermined level of plasticity and then vacuum forming the dental appliance to the model with the use of a vacuum forming table and a novel readaptation apparatus.

Figure 7:
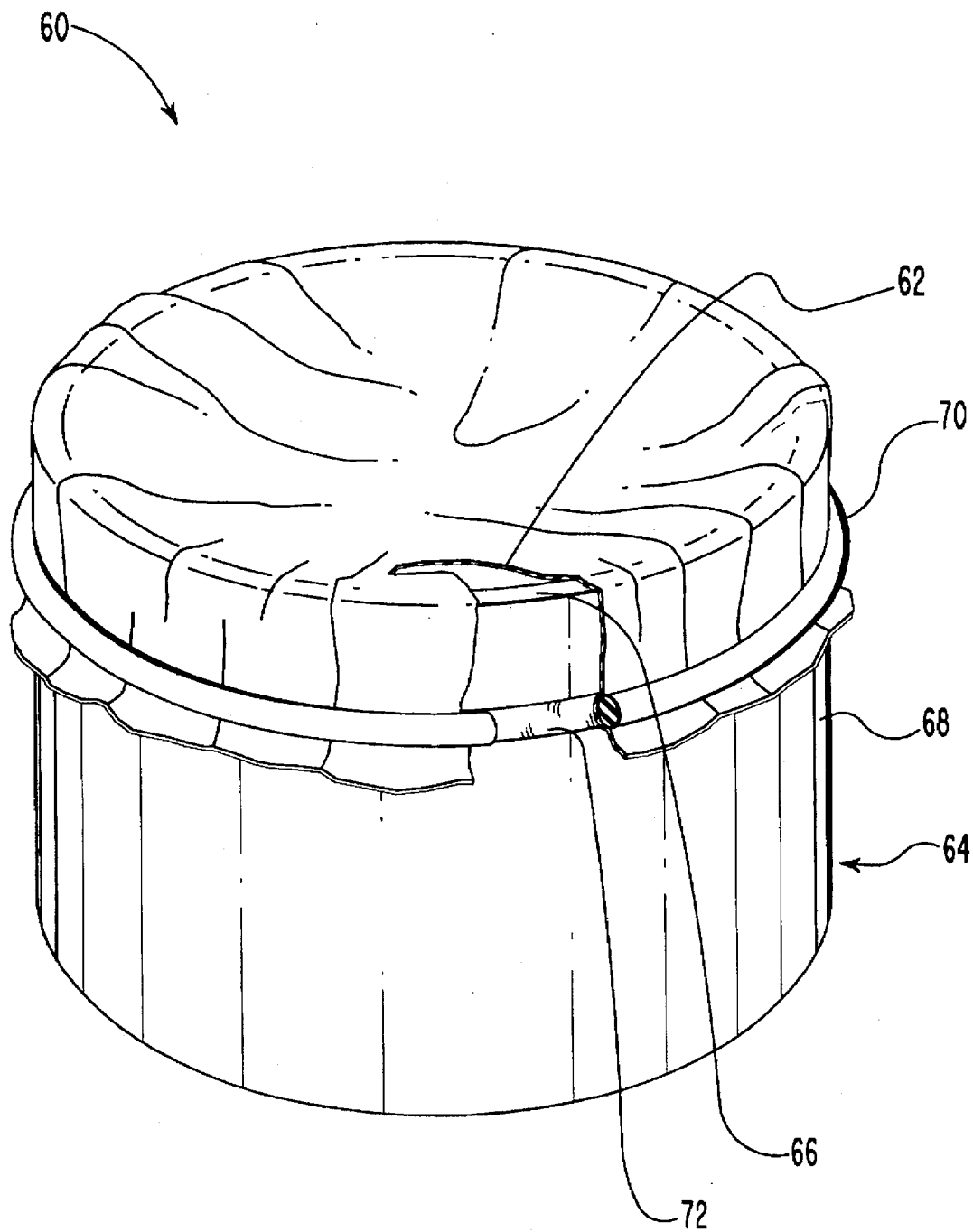
FIG. 7 is a perspective view of the readaptation apparatus of the present invention with a cutaway view showing the elastic membrane, the planar rim surface, and the groove beneath the clamping device.

The readaptation apparatus of the present invention comprises means for pressing the dental appliance closely to the contours and embrasures of the model upon application of negative pressure to the model. In the embodiment shown in FIG. 7, the pressing means comprises an elastic membrane. Also provided as part of the present invention is means for substantially sealing the elastic membrane to the surface of a vacuum forming table in order to sustain a negative pressure around the dental appliance and model. In the embodiment of FIG. 7, the sealing means comprises a drum head adapter 64. The drum head adapter 64 is formed with a planar rim surface 66 to which the elastic membrane 62 is attached, and which is used to seal the outer periphery of the elastic membrane 62 to the vacuum forming table. A sidewall 68 extending from the planar rim surface 66 provides a means for gripping the readaptation apparatus 60.

Figure 10:
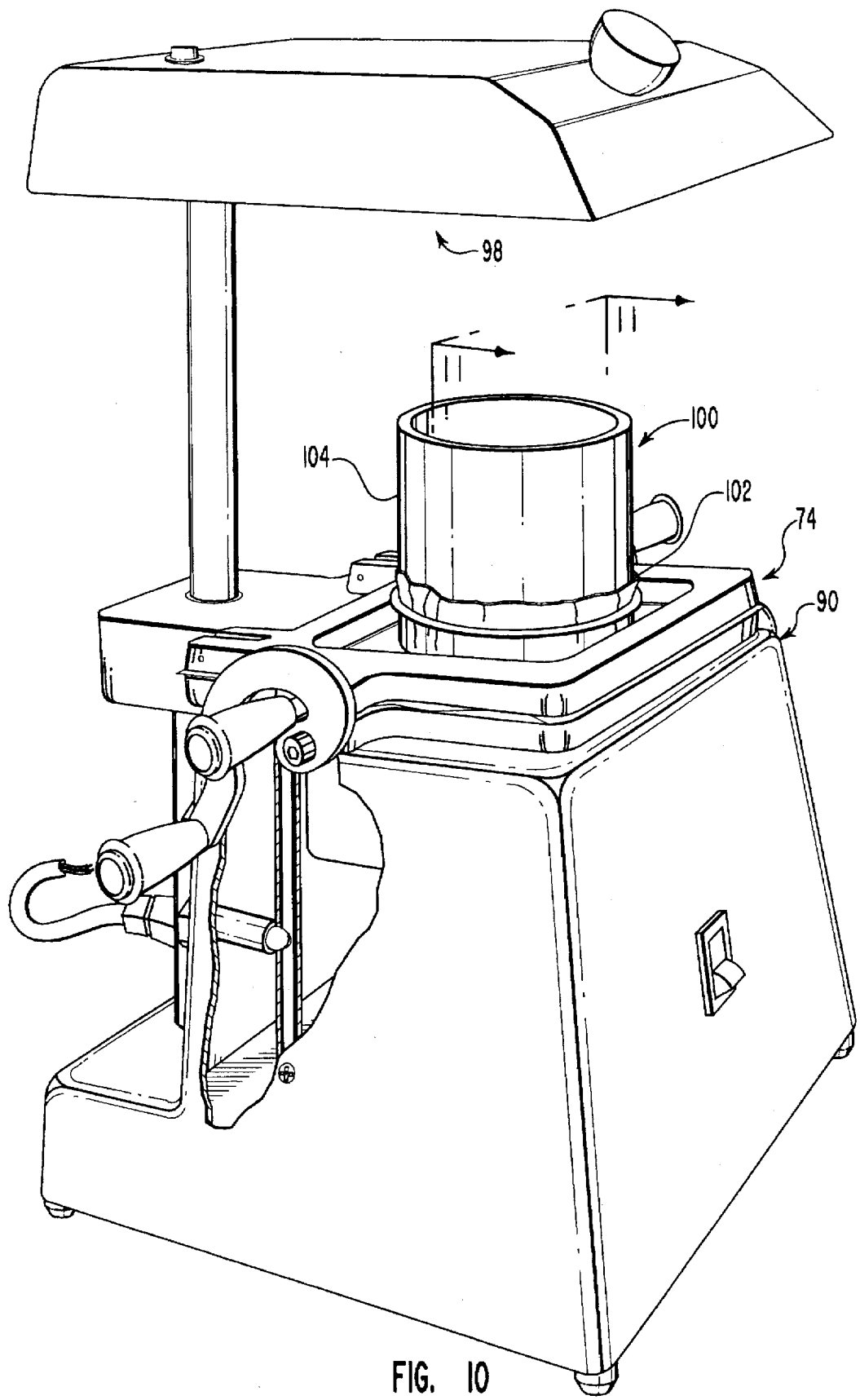
FIG. 10 is a perspective view showing the vacuum forming device of the present invention with a cutaway view of the guide rod and spring-loaded ball, and also showing the readaptation apparatus in position for readapting a dental appliance on the vacuum forming table.
Figure 11:
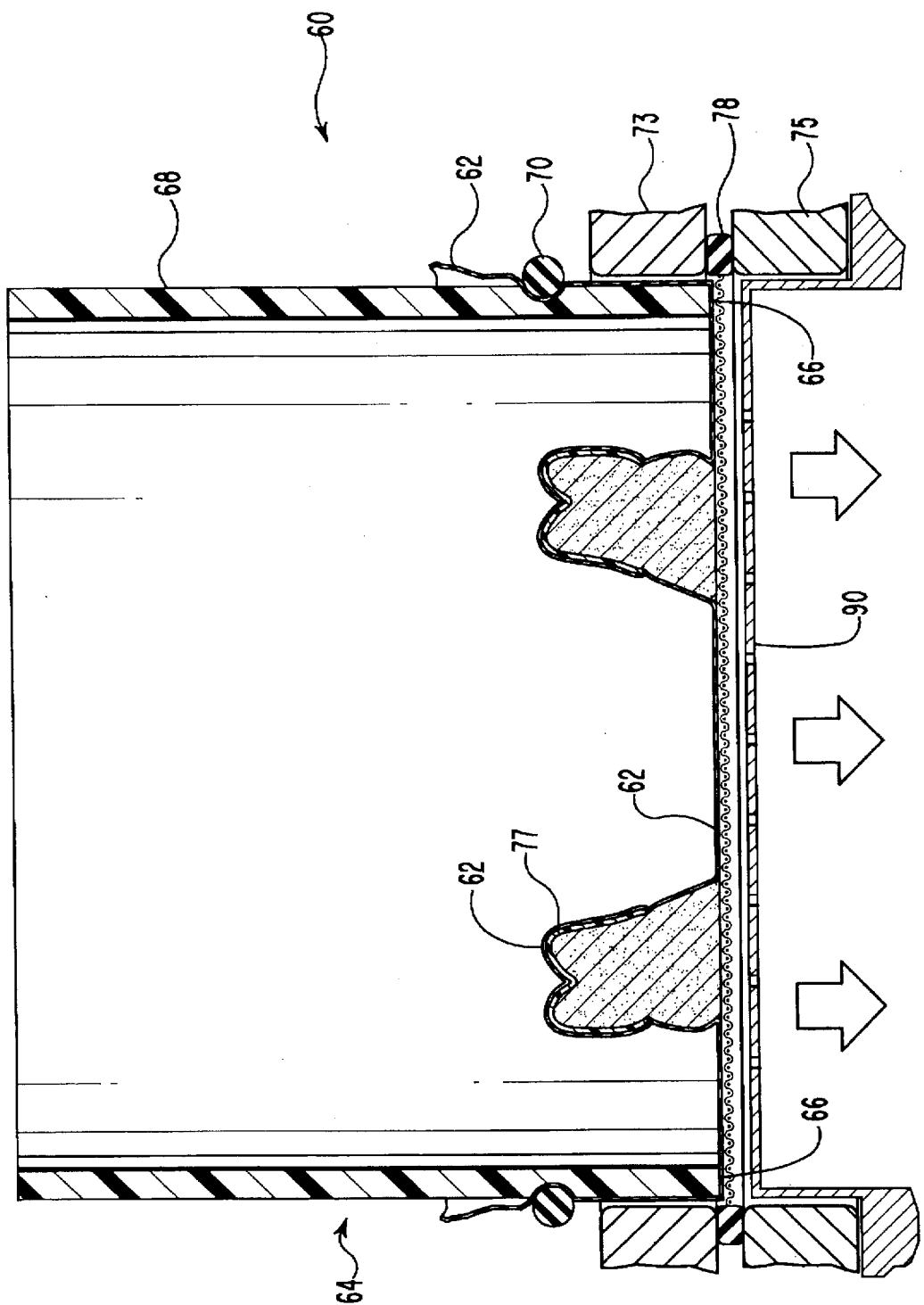
FIG. 11 is a cross sectional view of the readaptation apparatus taken at line 11—11 of FIG. 10, and shows the readaptation apparatus in position on the vacuum forming table over the model and dental appliance. Arrows represent the negative pressure generated by the vacuum forming table. The negative pressure is shown drawing the rubber membrane over the model, and closely conforming the appliance to teeth represented on the model.
Figure 1:
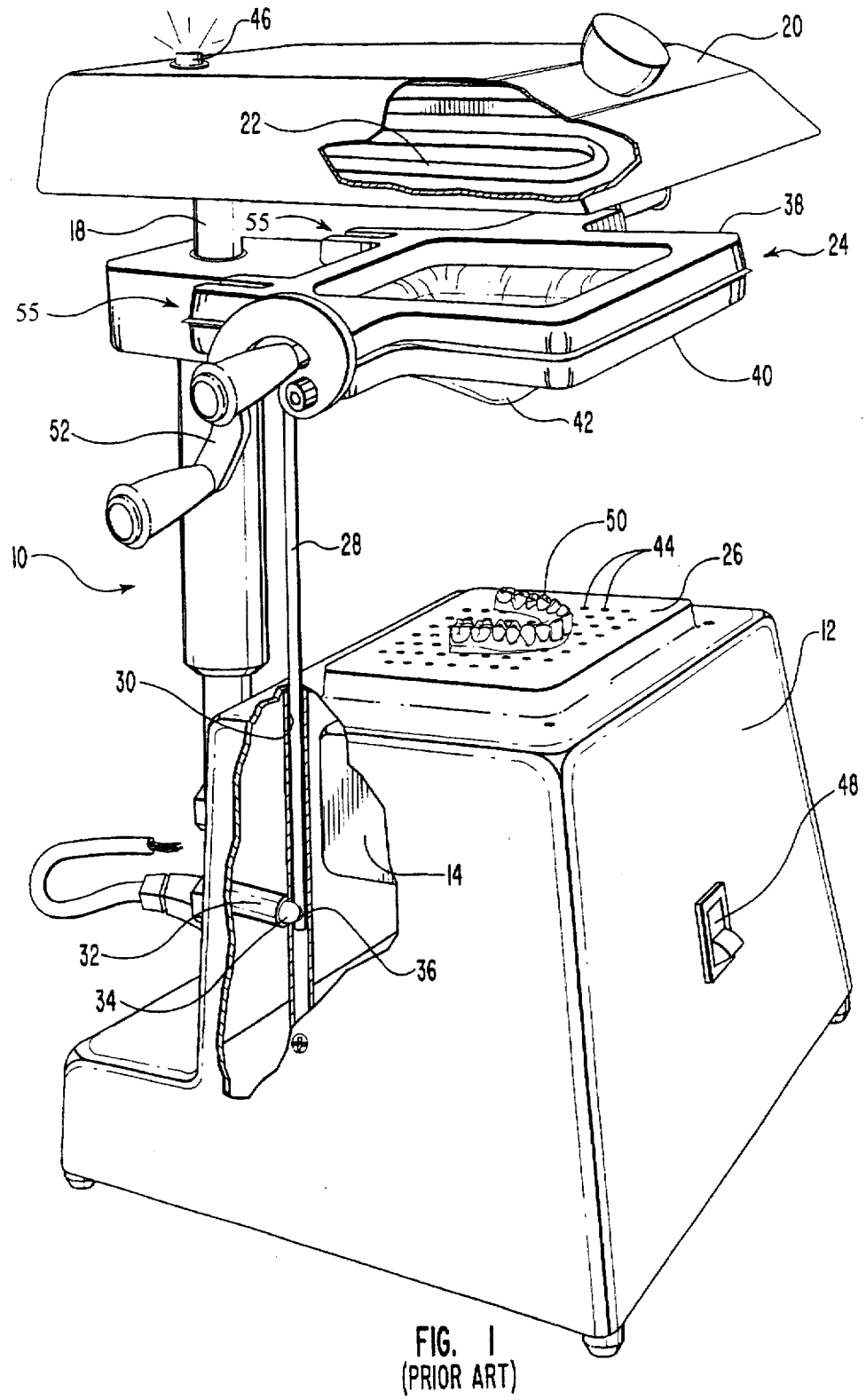
Figure 2:
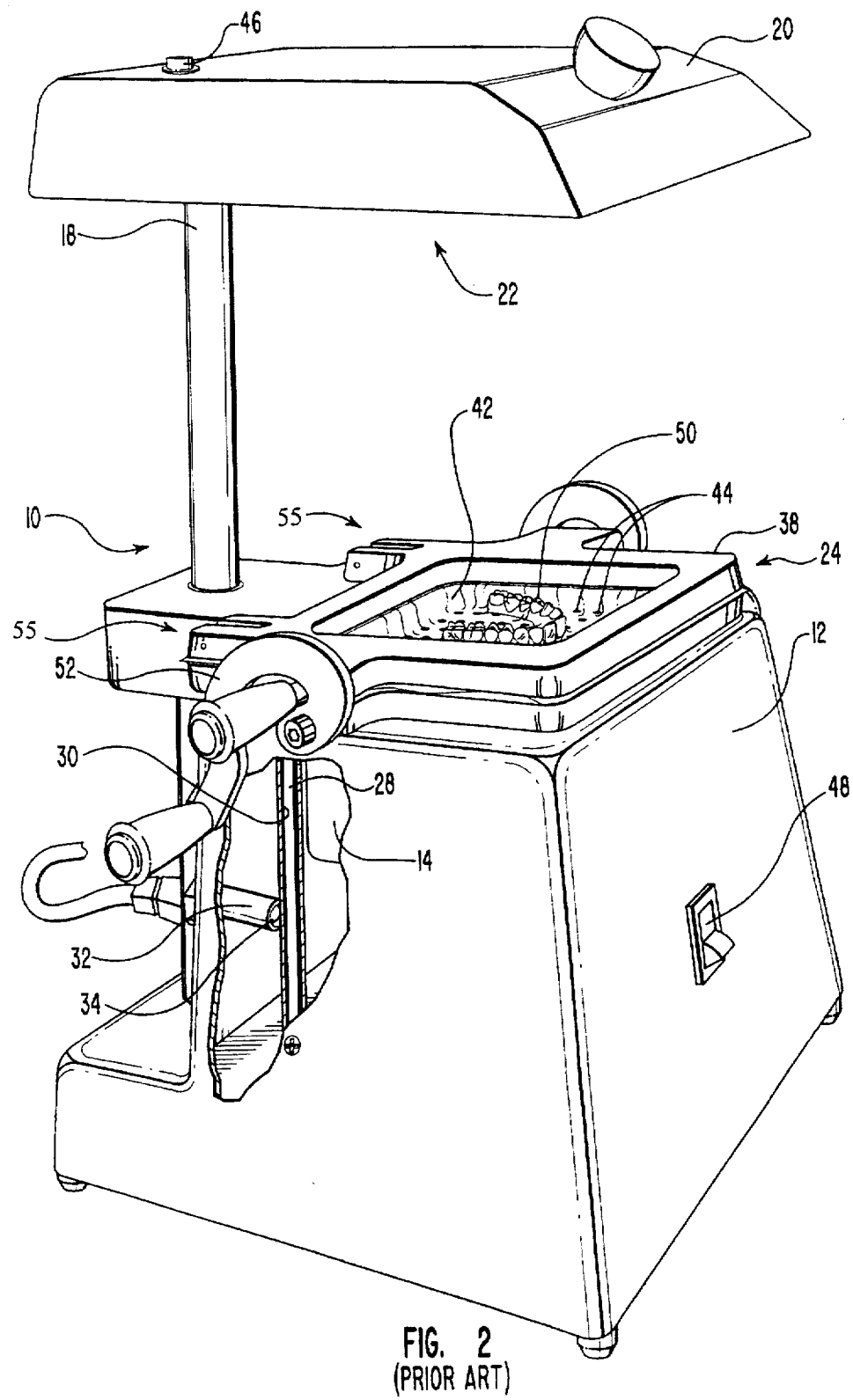

With the use of the drum head adapter 64, the elastic membrane 62 can be placed over the model 76, with the outer periphery of the elastic membrane 62 uniformly held to the surface of the vacuum forming table 90. Such an arrangement is shown in FIGS. 10 and 11. This is helpful in forming a substantially air tight seal with the vacuum forming table 90 in order to generate sufficient negative pressure around the dental appliance 77 and the model 76 to achieve readaptation.

Also provided are means for fastening the elastic membrane 62 to the planar rim surface 66. In the embodiment of FIG. 7, the fastening means comprises a rubber clamp 70 extending around the sidewall 68 adjacent to the planar rim surface 66. The fastening means could also comprise a hose clamp or other comparable fastener. A groove 72 can be used to locate the fastening means.

The sidewall 68 extends a distance from the planar rim surface 66, and has a top portion grippable by a human hand. The planar rim surface 66 is preferably flat to form a proper seal with the surface of the vacuum forming table 90. It should be noted that this embodiment is taught by way of example and is not intended to be restrictive. For instance, it should be seen that other means could be used by those skilled in the art to retain the edges of the elastic membrane to the vacuum forming table. As an example, if the vacuum forming table is contoured, rather than flat, the rim surface could also be of a corresponding contour.

The elastic membrane 62 is preferably relatively thin and highly elastic. A thin rubber dam, as commonly used in various other dental procedures, is the presently preferred material.

The elastic membrane 62 should be attached loosely to the retaining means in order to allow a given amount of sag at the center of the elastic membrane 62 such that when a model with representations of teeth is used, the elastic membrane will properly be drawn, along with the dental appliance, into the contours and embrasures of the represented teeth. As an example of proper calibration of the tension on the presently preferred embodiment, a weight approximating that of a U.S. quarter placed on the elastic membrane, which is attached to an annular rim surface of about four inches in diameter, should cause the center of the elastic membrane to drop below the edges of the elastic membrane 62 a distance of approximately ⅞ of an inch. FIG. 7 shows an elastic membrane attached to the retaining means with an appropriate amount of sag.

The system of the present invention comprises the above-described readaptation apparatus, and in addition comprises a vacuum forming device similar to that described in the Relevant Technology Section, above. In accordance with the present invention, the basic vacuum forming device of the prior art is enhanced with certain new and inventive features in order to accommodate the inventive method and system, as will be explained and shown in FIGS. 8 through 10. First, it is necessary that the vacuum forming device be provided with a means for positioning the model and dental appliance in a predetermined position relative to the heating element. Also, it has been found to be necessary when readapting a dental appliance that less heat be applied to the dental appliance than during the original adaptation procedure. This is because it is desirable for the appliance to retain its adapted shape and not be deformed. Sufficient heat must be applied to bring the dental appliance to a desired level of plasticity, but not to the point of melting. Therefore, when using the vacuum forming device with a built in heating element, the appliance must be held in a position further away from the heating element than that used to initially heat the thermoplastic sheet. This requires that the positioning means also be able to locate the model and dental appliance in the proper location a correct distance from the heat source. In the embodiment depicted in FIGS. 8 and 9, the means for positioning the model and dental appliance with respect to the heating element and vacuum forming table comprises a clamping flame 74.

In order to support the model 76 on the clamping frame 74, a retaining screen 78 is used that is of sufficient dimensions to fit within the clamping frame 74. The clamping frame 74 consists of an upper frame 73 and a lower frame 75. Clamps 80 on the clamping frame are used to hold the upper frame 73 and the lower frame 75 together, with the retaining screen 78 interposed between them. In the presently preferred embodiment, the retaining screen 78 is formed from a wire mesh that will support the model 76 and dental appliance 77, while still allowing negative pressure from below to reach the model 76 and dental appliance 77.

Figure 8:
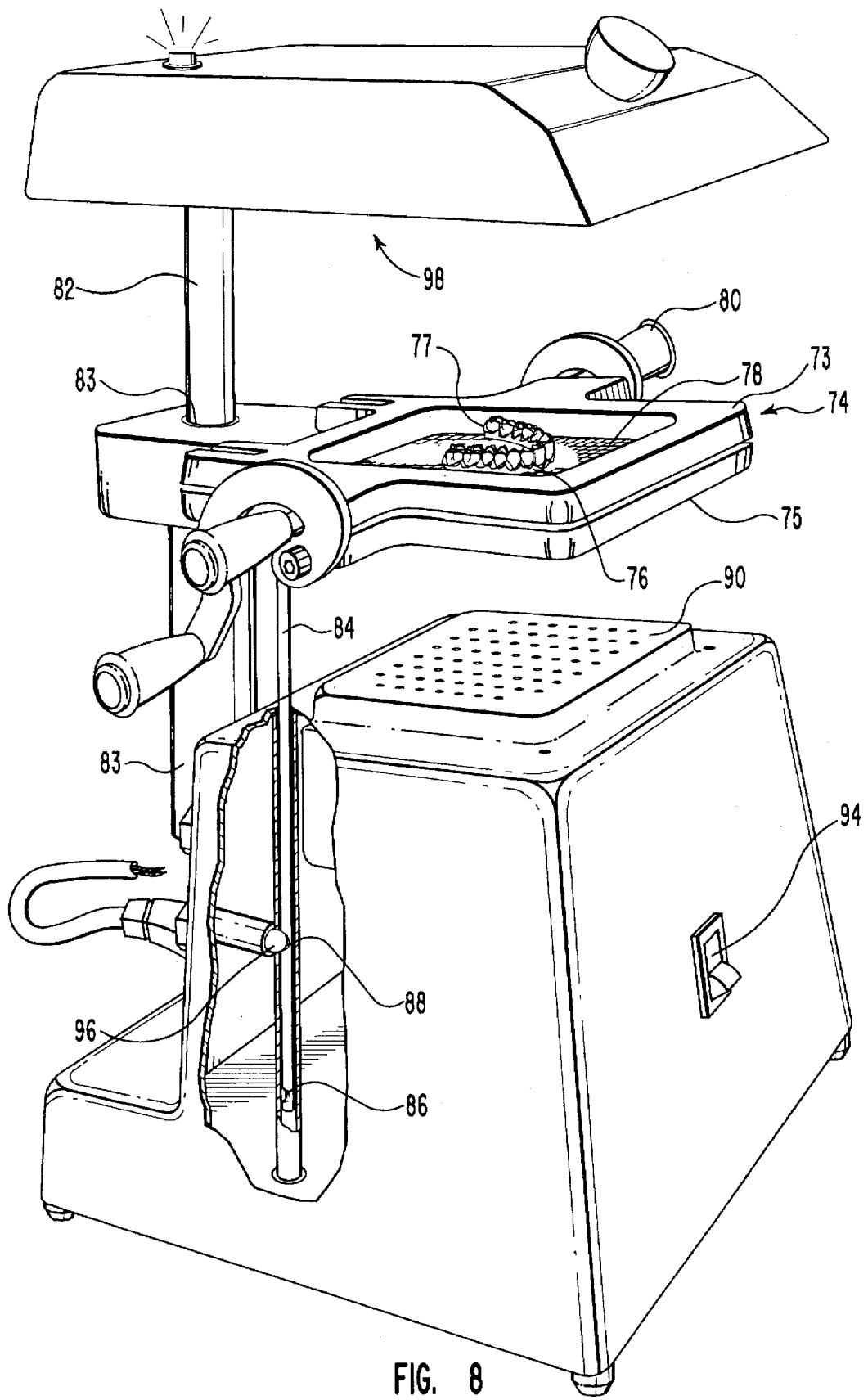
FIG. 8 is a perspective view of the vacuum forming device of the present invention, with a cutaway view showing the guide rod and spring-loaded ball, and the first and second indentations on the guide rod. The clamping flame is shown holding the dental appliance and model on the retaining screen in the proper position for heating the dental appliance prior to readaptation.

Also used as part of the present system is a means for relocating the model and dental appliance from a first predetermined position, which is a proper distance from the heat source for the readaptation procedure, to a second predetermined position resting on the vacuum forming table. In the embodiment of FIGS. 8 and 10, the relocating means comprises a glide rail 82 and a guide rod 84. The clamping frame 74 is attached by means of a slidable sleeve 83 to the glide rail 82, which extends between the heating element 98 and the vacuum forming table 90. The guide rod 84 is provided with a first indentation 86 for use in the original adaptation procedure, and in accordance with the present invention, a second indentation 88 for receiving the spring-loaded ball mechanism 96 is also provided. The second indentation 88 is located above the first indentation 86. Thereby, the clamping frame 74 may be located at a position further away from the heating element 98 than when the dental appliance 77 was originally formed. Using the positioning means and the relocating means, the model 76 and dental appliance 77 are easily positioned a proper distance from the heating source 98, and when ready to be readapted, are readily repositioned onto the vacuum forming table 90. With the use of the convenient relocating means thus described, delays between heating and vacuum forming are minimized, maintaining the proper plasticity of the dental appliance 77.

As will be evident to one skilled in the art, other means may be used for positioning the model 76 and appliance 77 at the desired position. For instance, in the embodiment of FIG. 9, a support frame 74, is shown resting on the vacuum forming table 90, for positioning the model 76 and dental appliance 77 relative to the heating element 90. The support frame 74 could also be of other shapes and could also be rested on the ground.

Figure 3:
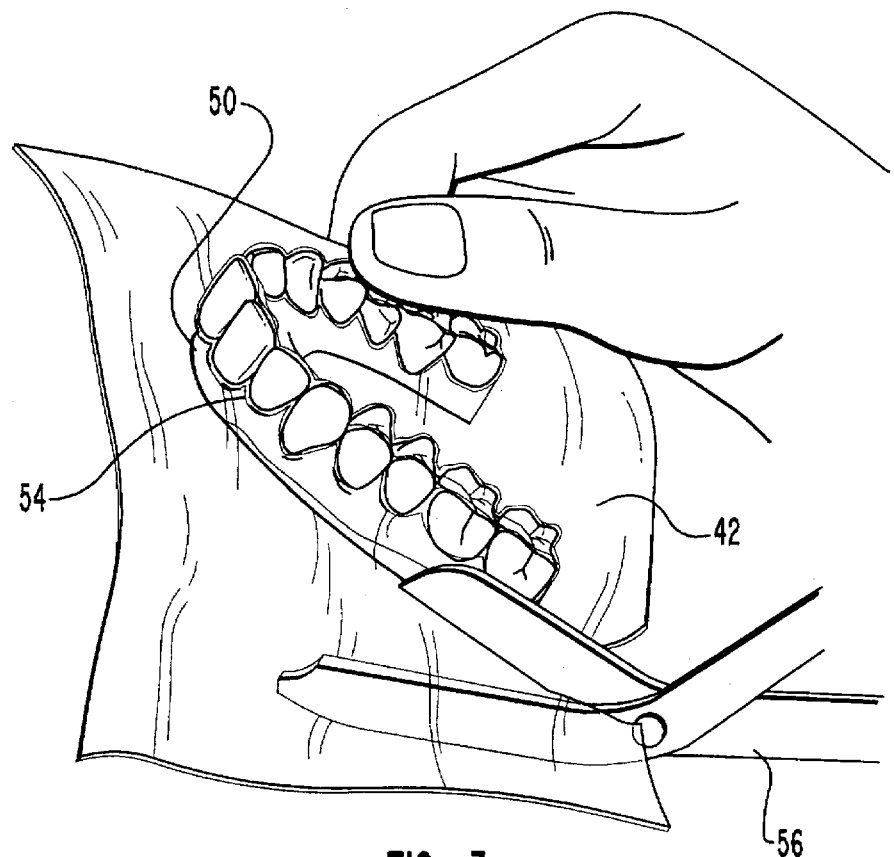
FIG. 3 is a perspective view of a model with an adapted dental appliance that has been formed using the vacuum forming device of FIGS. 1 and 2 positioned on the model. The dental appliance is undergoing the process of having the excess plastic trimmed from its edges.
Figure 4:
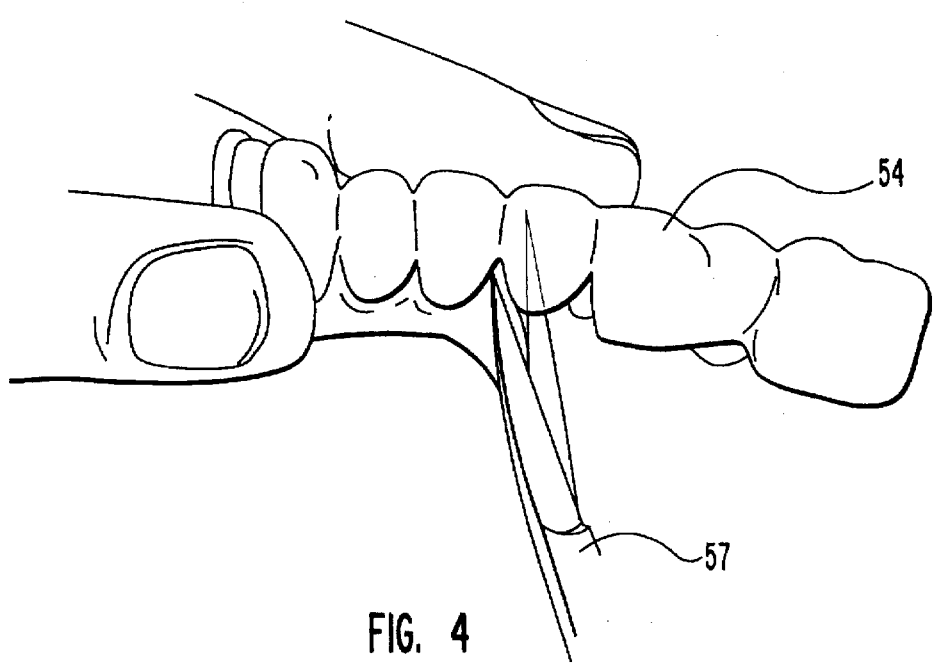
FIG. 4 is a perspective view of the dental appliance of FIG. 3. The dental appliance of FIG. 3 has been removed from the model and is shown undergoing further trimming of the excess plastic.

A method of readaptation using the above described apparatus and system is also part of the present invention and comprises the following steps. First, the dental appliance is formed in the shape of the teeth to which it is to be applied, preferably using the method of vacuum forming described in The Relevant Technology Section, above. Once adapted, the dental appliance is removed from the model, and the excess plastic is trimmed from around the dental appliance, as shown in FIGS. 3 and 4. Removing and trimming the appliance can be accomplished much more easily under the present invention, because great care need not be taken to prevent distortion. For instance, the dental appliance may be turned inside out for trimming. Also, cuts can be made deeply into corners and embrasures between the teeth. This saves time in the adaptation stage.

Readaptation is accomplished by setting the appliance back into place over the model, and then placing the model into position on the vacuum forming device as shown in FIG. 8. In doing so, and in accordance with the embodiments taught above, the retaining screen 78 is inserted into the clamping frame 74 and is secured in place by engaging the clamps 80. The model 76 and dental appliance 77 are then placed, with the teeth pointing up, on the retaining screen 78. The heating element 98 is then enabled by pressing switch 94, and the clamping frame 74 is placed in the proper readaptation position with respect to the heating element, where the spring-loaded ball mechanism engages the second indentation 88.

Figure 5:
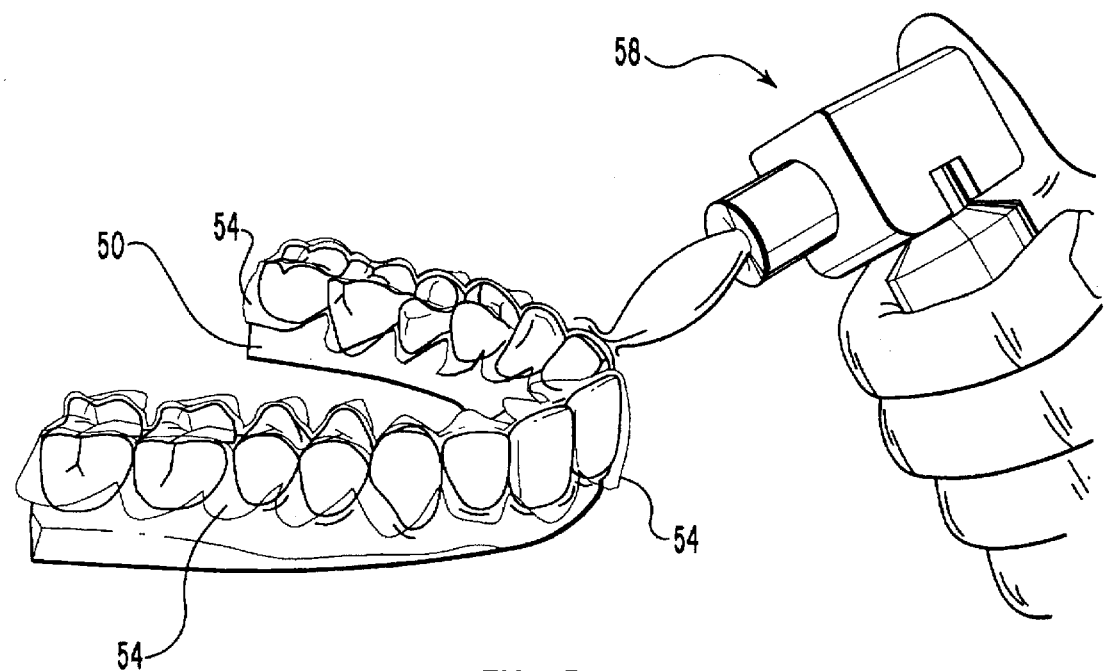
FIG. 5 is a perspective view of a dental appliance positioned on a model. The dental appliance is shown undergoing a process of being heated with a flame torch.
Figure 6:
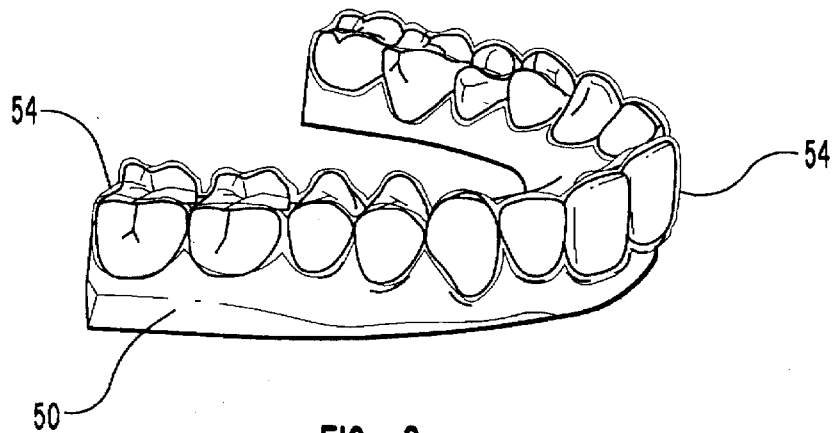
FIG. 6 is a perspective view of a dental appliance shown positioned on a model and displaying the closer fit provided by readaptation procedures.
Figure 9:
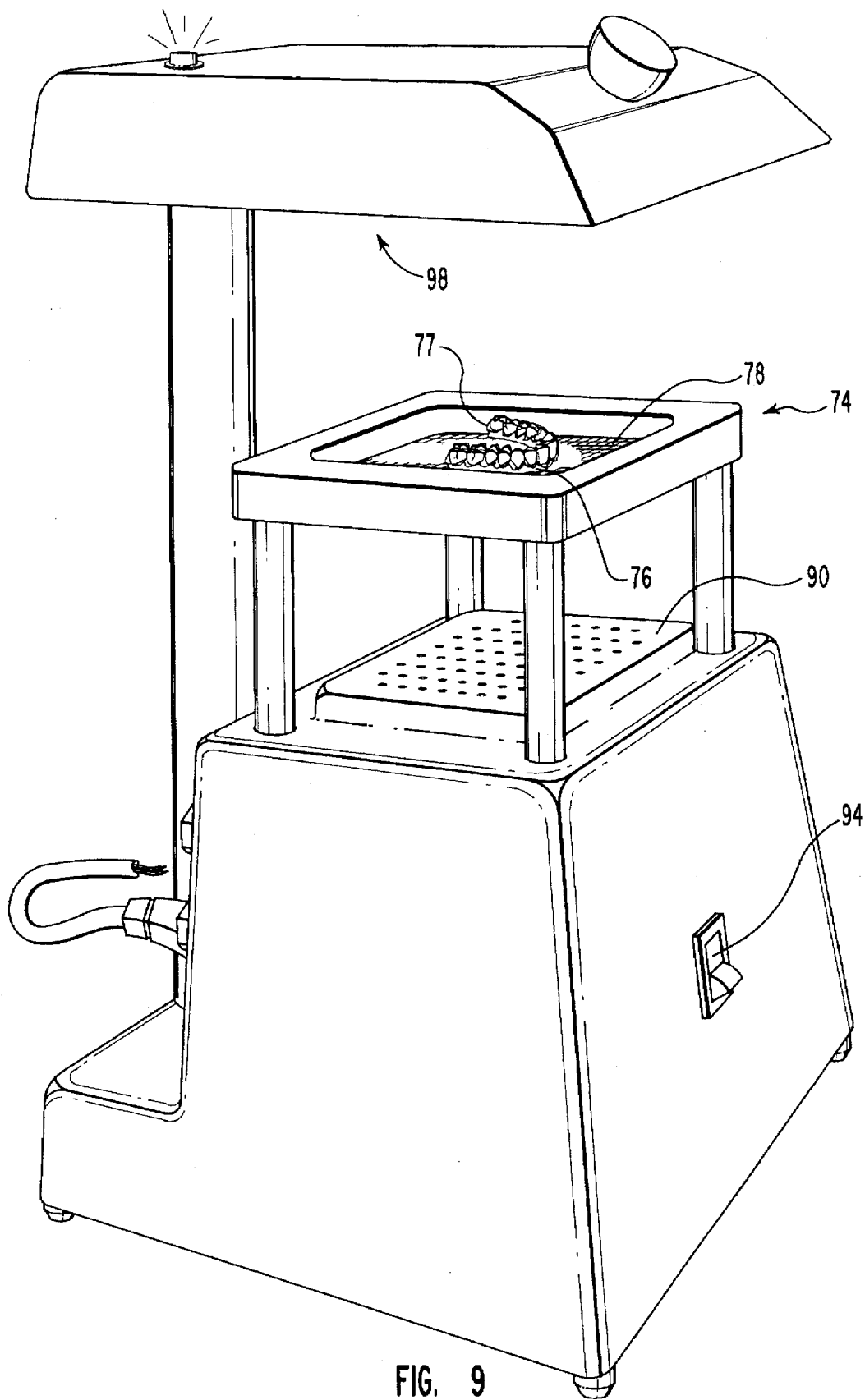
FIG. 9 is a view of a further embodiment of the vacuum forming device of the present invention showing a positioning flame resting on the vacuum forming table and being used to position the dental appliance and model in the proper position for heating.

In the embodiment of FIG. 9, the model 76 and dental appliance 77 are placed in the proper position relative to the heating element 98 by resting them on the support frame 74. The support frame 74 is then placed on top of the vacuum forming table 90 and the heating element 98 is enabled. Alternately, the step of heating the dental appliance 77 to a state of plasticity could be accomplished with an independently located heating device, or with the use or a flame torch as depicted in FIG. 5.

Under the embodiment of FIG. 8, the second indentation 88 on the guide rod 84 is utilized to receive the spring-loaded ball mechanism 96. The second indentation 88 is located such that the clamping frame 74 will be maintained in the proper vertical position, holding the model 76 further away from the heating element 98 than the original adaptation position, which is preferably locatable with the first indentation 86. The heating element 98 is then operated for a sufficient amount of time to achieve a sufficient level of plasticity of the dental appliance 77, which time is a function of the heat of the heating element 98, the distance of the clamping frame 74 from the heating element 98, and the time in which the heating element 98 is enabled. As an example, using a 550 Watt heating element from a cold start at a distance of about three and a half inches from the heating element 98 to the retaining screen 78, the dental appliance 77 should be exposed to the heat for a period of about three minutes. From a warm start, the dental appliance 77 should be exposed from about one to two minutes, depending on the time the heating element 98 has had to cool.

A timer, thermostat, or other means may be used to determine when the dental appliance 77 has reached the point of sufficient plasticity. Once the dental appliance 77 is sufficiently heated, the model 76 and dental appliance 77 are returned to the vacuum forming table 90. With the embodiment taught above, this comprises merely exerting sufficient downward pressure on the clamping frame 74 to release the spring-loaded ball mechanism 96 from its position in the second indentation 88, and pulling the clamping frame 74 down into a resting position on the vacuum forming table 90.

As shown in FIGS. 10 and 11, the readaptation device 60 is then used to sustain a negative pressure around the model 76 and dental appliance 77, to conform the dental appliance 77 closely to the contours and embrasures of teeth represented on the model 76. In accordance with the embodiment described above, this comprises placing the elastic membrane 62 of the readaptation device 60 over the model 76 and the dental appliance 77 as shown. This is done by grasping the top of the sidewall 68 of the drum head adapter 64, placing the elastic membrane 62 over the model 76 and dental appliance 77, and pressing the planar rim surface 66 and the outer periphery of the elastic membrane 62 to the vacuum forming table 90. The vacuum pump is then activated for a sufficient amount of time until the dental appliance 77 cools. Once again, a timer or thermostat may be used to determine the proper amount of time for readaptation and cooling. The vacuum pump is then switched off and readaptation is complete. The dental appliance 77 is allowed to completely cool and is removed from the model 76. Removal causes little distortion after readaptation, as the excess plastic has already been trimmed from the dental appliance 77. After readaptation, the dental appliance should fit snugly to the model.

The inventive process achieves readaptation much more quickly than that of the prior art, substantially reducing the cost of these procedures. Furthermore, the readapted dental appliance 77 formed in accordance with the present invention will conform much more closely to the teeth, such that it can be worn more comfortably, without irritating the gums, and will be better retained on the teeth. Also, the invention provides for more accurate carrier trays, with better control of procedures introducing a material into the mouth for prolonged periods of time. This expands the range of materials that may be introduced, and lowers the cost of such procedures. Thus, when applications such as treating the teeth or gums or whitening the teeth are used, medicine or other substances held within the appliance will more properly maintain their position in the dental appliance 77 and will not substantially leak out of the dental appliance 77.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for use in readapting a previously formed dental appliance to closely conform to the contours and embrasures of a model representative of a patient's teeth, wherein the dental appliance has first been heated to attain a predetermined level of plasticity, the apparatus comprising:
   a. a vacuum forming table, comprising means for generating a negative pressure: and
   b. elastic membrane means responsive to the negative pressure for pressing the dental appliance against the model with sufficient force to cause the dental appliance to conform to the contours and embrasures of the model and for maintaining the dental appliance in close contact with the model until the dental appliance cools an amount sufficient to retain its shape and the negative pressure is released.

2. An apparatus as recited in claim 1, wherein the elastic membrane comprises a thin rubber dam.

3. An apparatus as recited in claim 1, wherein the pressing means further comprises means for substantially sealing the outer periphery of the elastic membrane against the surface of the vacuum forming table.

4. An apparatus as recited in claim 3, wherein the sealing means comprises a substantially planar rim surface for uniformly contacting the vacuum forming table and means for fastening the elastic membrane to the substantially planar rim surface.

5. An apparatus as recited in claim 4, wherein the sealing means further comprises a substantially annular side wall extending from the rim surface, the substantially annular sidewall having a top portion suitable for being received within a human hand.

6. An apparatus as recited in claim 3, wherein the sealing means comprises a drum head adapter having a substantially planar rim surface, with the elastic membrane being attached to the substantially planar rim surface, and wherein the tension on the elastic membrane is sufficiently low that the elastic membrane will cause the dental appliance to conform to the contours and embrasures of the teeth represented on the model upon application of negative pressure to the dental appliance and model.

7. An apparatus for use in readapting a dental appliance to closely conform to the contours and embrasures of a model representative of a patient's teeth, wherein the dental appliance has first been heated to attain a level of plasticity, the apparatus comprising:
   a. a vacuum forming table, comprising means for generating a negative pressure; and
   b. an elastic membrane responsive to the negative pressure for pressing the dental appliance against the model with sufficient force to cause the dental appliance to conform to the contours and embrasures of the model, and for maintaining the dental appliance in close contact with the model until the dental appliance cools an amount sufficient to retain its shape.

8. An apparatus as recited in claim 7 further comprising means for substantially sealing the outer periphery of the elastic membrane against the surface of the vacuum forming table.

9. An apparatus as recited in claim 8 wherein the sealing means comprises a substantially planar rim surface for uniformly contacting the vacuum forming table and means for fastening the elastic membrane to the substantially planar rim surface.

10. An apparatus as recited in claim 9, wherein the sealing means comprises a drum head adapter having formed thereon the substantially planar rim surface, the drum head adapter further comprising a substantially annular sidewall extending from the substantially planar rim surface, the elastic membrane being connected to the substantially planar rim surface by the fastening means in a manner exerting a low tension on the elastic membrane.

11. An apparatus as recited in claim 10, wherein the elastic membrane comprises a thin rubber dam.

12. An apparatus for use in a procedure of readapting a dental appliance to closely conform to the contours and embrasures of a model representative of a patient's teeth, wherein the dental appliance has first been heated to attain a predetermined level of plasticity, the apparatus comprising:
   a. a vacuum forming table provided with a vacuum pump for generating a negative pressure on a surface of the vacuum forming table;
   b. an elastic membrane;
   c. a drum head adapter, the drum head adapter comprising:

i. a substantially planar rim surface for uniformly contacting the vacuum forming table, and ii. a substantially annular side wall extending from the substantially planar rim surface, the substantially annular sidewall having a top suitable for being received within a human hand; and d. a clamp fitted around the substantially annular sidewall, proximal to the substantially planar rim surface, with the elastic membrane interposed between the clamp and the substantially annular sidewall in a manner exerting a low tension on the elastic membrane, such that the elastic membrane will respond to the negative pressure by pressing the dental appliance to the model, causing the dental appliance to closely conform to the contours and embrasures of the teeth represented on the model.

13. A system for use in readapting a previously formed dental appliance to closely conform to the contours and embrasures of a model representative of a patient's teeth, wherein the dental appliance has first been heated to attain a predetermined level of plasticity, the apparatus comprising:

a. means for generating a negative pressure:

b. a support surface on which the model and dental appliance can be supported and exposed to the negative pressure: and c. elastic membrane means responsive to the negative pressure liar pressing the dental appliance against the model with sufficient force to cause the dental appliance to conform to the contours and embrasures of the model and the maintaining the dental appliance in close contact with the model until the dental appliance cools an amount sufficient to retain its shape and the negative pressure is released.

14. A system as recited in claim 13, wherein the support surface comprises a vacuum forming table, and wherein the negative pressure generating means comprises a vacuum pump.

15. A system as recited in claim 13, further comprising a heating element capable of heating the dental appliance to the predetermined level of plasticity.

16. A system as recited in claim 15, further comprising means for positioning the model and dental appliance in at least one predetermined position relative to the heating element.

17. A system as recited in claim 16, wherein the positioning means is capable of positioning the model and dental appliance in two separate predetermined positions relative to the heating element.

18. A system as recited in claim 16, wherein the positioning means comprises a clamping frame locatable in the at least one predetermined position relative to the heating element.

19. A system as recited in claim 18, wherein the positioning means further comprises a retaining screen attachable to the clamping frame, the retaining screen being suitable for supporting the model and dental appliance thereon and for allowing negative pressure to reach the model and dental appliance when the clamping frame is positioned in proximity to the support surface and exposed to the negative pressure.

20. A system as recited in claim 19, wherein the positioning means further comprises a glide rail extending between the support surface and the heating element, and wherein the clamping frame is movably connected to the glide rail, such that the clamping frame may be relocated between the first predetermined position and a second predetermined position in close proximity to the support surface.

21. A system as recited in claim 20, wherein the positioning means further comprises:

a. a guide rod for use in relocating the clamping frame between the first and second predetermined positions, the guide rod having a first end and a second end, the first end being attached to the clamping frame and the second end being dynamically located in a sleeve fixed with respect to the vacuum forming table, the guide rod having a surface with at least one indentation formed therein; and b. a spring-loaded ball mechanism for being received into the at least one indentation and capable of being held in the at least one indentation with sufficient force to temporarily maintain the clamping frame in the first predetermined position.

22. A system as recited in claim 18, wherein the clamping frame comprises:

a. an upper frame;

b. a lower frame; and c. at least one hinge connecting the upper frame to the lower frame.

23. A system as recited in claim 22 further comprising at least one S-shaped clamp, wherein the upper frame and lower frame are securable together with the at least one S-shaped clamp.

24. A system as recited in claim 13, wherein the elastic membrane comprises a thin rubber dam.

25. A system as recited in claim 13, further comprising means for substantially sealing the outer periphery of the elastic membrane against the support surface.

26. A system as recited in claim 25, wherein the sealing means comprises a substantially planar rim surface and means for fastening the elastic membrane to the substantially planar rim surface.

27. A system as recited in claim 26, wherein the sealing means comprises a substantially annular sidewall extending from the substantially planar rim surface, the substantially annular sidewall having a top portion suitable for being received within a human hand.

28. A system as recited in claim 25, wherein the sealing means further comprises a drum head adapter, the drum head adapter having a substantially planar rim surface, with the elastic membrane being connected to the substantially planar rim surface in a manner exerting a low tension on the elastic membrane, such that the elastic membrane will respond to the negative pressure by pressing the dental appliance to the model, and causing the dental appliance to closely conform to the contours and embrasures of the teeth represented on the model.

29. A system for readapting a dental appliance to closely conform to the contours and embrasures of a model representative of a patient's teeth, wherein the dental appliance is first heated to a level of plasticity, the system comprising:

a. means for generating a negative pressure;

b. a vacuum forming table having a surface on which the model and dental appliance can be supported and exposed to the negative pressure;

c. a heating element disposed a predetermined distance from the vacuum forming table;

d. means for positioning the model and dental appliance in a first predetermined location, the first predetermined location being a given distance from the heating element;

e. means for relocating the positioning means from the first predetermined position to a second predetermined position in close proximity to the surface of the vacuum forming table; and f. an elastic membrane for pressing the dental appliance to the model in response to the negative pressure.

30. A system as recited in claim 29, wherein the positioning means further comprises:

a clamping frame; and a retaining screen for being clampably held within the clamping frame, the retaining screen being suitable for holding the model in position on the clamping frame and for allowing negative pressure to reach the model when the clamping frame is positioned in proximity to the support surface.

31. A system as recited in claim 30, wherein the relocating means further comprises:

a. a glide rail extending between the vacuum forming table and the heating element, with the clamping frame being movably connected to the glide rail;

b. a guide rod having a first end and a second end, the first end being attached to the clamping frame and the second end being dynamically inserted into a sleeve fixed with respect to the vacuum forming table, the guide rod having a surface with at least one indentation formed therein; and c. a spring-loaded ball mechanism for being received into the at least one indentation and of being held in the at least one indentation with a sufficient force to temporarily maintain the clamping frame in the first predetermined position.

32. A system for readapting a dental appliance to closely conform to the contours and embrasures of a model representative of a patient's teeth, wherein the dental appliance is first heated to a level of plasticity, the system comprising:

a. a vacuum forming device, comprising:
   i. a vacuum pump for generating a negative pressure;
   ii. a body section, with the vacuum pump being disposed within the body section;
   iii. a vacuum forming table located at the top of the body section, the vacuum forming table having a surface linked in negative pressure communication with the vacuum pump;
   iv. a heating element capable of heating the dental appliance to a level of plasticity;
   v. a hood disposed above the body section, with the heating element being contained in the hood;
   vi. a clamping frame dynamically displacable between a first predetermined position a given distance from the hood and a second predetermined position in close proximity to the vacuum forming table, the clamping frame comprising:
      (1) an upper frame;
      (2) a lower frame;
      (3) at least one hinge connecting the upper frame to the lower frame; and
      (4) at least one S-shaped clamp, wherein the upper frame and lower frame are securable together with the at least one S-shaped clamp;
   vii. a retaining screen for being clampably held within the clamping frame, the retaining screen being suitable for holding the model in position on the clamping frame and for allowing negative pressure from below to reach the model and dental appliance when the clamping frame rests on the support surface;
   viii. a glide rail extending between the body section and the hood, with the clamping frame being displacably connected to the glide rail;
   ix. a guide rod having a first end and a second end, the first end being attached to the clamping frame and the second end being displacably inserted into a sleeve in the body section, the guide rod having a surface with at least one indentation formed therein; and
   x. a spring-loaded ball mechanism for being received into the at least one indentation, and of being held in the at least one indentation with a sufficient force to temporarily maintain the clamping frame in the first predetermined position; and b. a readaptation device, comprising:
   i. an elastic membrane, the elastic membrane being adapted for being placed over the model and dental appliance when the model and dental appliance are located on the vacuum forming table; and
   ii. a drum head adapter, comprising:
      (1) a substantially planar rim surface, with the outer periphery of the elastic membrane being connected to the substantially planar rim surface;
      (2) a substantially annular sidewall extending from the substantially planar rim surface, the substantially annular sidewall having a top portion suitable for being received within a human hand; and
      (3) a clamp fitted around the outer periphery of the substantially planar rim surface, with the elastic membrane being interposed between the clamp and the substantially planar rim surface, such that the outer periphery of the elastic membrane is capable of being held to the vacuum forming table, and wherein the tension on the elastic membrane is sufficiently low that the elastic membrane will respond to the negative pressure by closely conforming the dental appliance to the contours and embrasures of the representative teeth of the model.

33. A method for readapting a previously formed dental appliance to closely conform to the contours and embrasures of a patient's teeth represented on a model, the method comprising the steps of:

a. placing the dental appliance on the model:

b. heating the dental appliance unlike the dental appliance reaches a predetermined level of plasticity;

c. placing an elastic membrane over the previously formed dental appliance and applying a negative pressure to the dental appliance and model and maintaining the negative pressure around the dental appliance and model such that the elastic membrane presses the dental appliance against the model with sufficient three to cause the dental appliance to closely conform to the contours and embrasures of the teeth represented on the model, maintaining the dental appliance in close contact with the model until the dental appliance cools an amount sufficient to retain its shape and the negative pressure is removed.

34. A method as recited in claim 33, wherein the step of applying a negative pressure to the dental appliance and model further comprises covering the dental appliance and model with an elastic membrane.

35. A method as recited in claim 34, wherein the elastic membrane is attached to a substantially planar rim surface for sealing the outer periphery of the elastic membrane to the support surface, the elastic membrane being attached to the substantially planar rim surface with a sufficiently low tension that the dental appliance will be caused to closely conform to the contours and embrasures of the teeth represented on the model.

36. A method as recited in claim 33, wherein the negative pressure is generated by a vacuum pump, and wherein the surface exposable to the negative pressure comprises a vacuum forming table linked in negative pressure communication with the vacuum forming table.

37. A method as recited in claim 33 wherein the step of heating the dental appliance further comprises the steps of:
   a. attaching a retaining screen to a clamping frame that is integrally and movably attached to the vacuum forming device;
   b. placing the model and dental appliance on the retaining screen;
   c. positioning the clamping frame a predetermined distance from a heating element, and
   d. exposing the dental appliance to heat from the heating element for a sufficient amount of time for the dental appliance to reach a predetermined level of plasticity.

38. A method as recited in claim 36, wherein the step of positioning the dental appliance and model on the surface of the vacuum forming device comprises relocating the clamping frame from the predetermined position relative to the heating element to a position in close proximity to the surface of the vacuum forming device.

39. A method as recited in claim 33, wherein the step of heating the dental appliance further comprises using a flame torch to bring the dental appliance to a proper state of plasticity.

40. A method as recited in claim 33 wherein the step of heating the appliance further comprises the steps of:
   a. placing the dental appliance and model on a support frame,
   b. positioning the support frame a predetermined distance from a heating element; and
   c. exposing the dental appliance to heat from the heating element for a sufficient amount of time for the appliance to achieve a predetermined level of plasticity.

41. A method as recited in claim 33, further comprising an adaptation process prior to readaptation comprising the steps of:
   a. heating a sheet of thermoplastic materials;
   b. forming the sheet of thermoplastic materials into a dental appliance on the vacuum forming table;
   c. removing the dental appliance from the model; and
   d. trimming the excess material of the sheet of thermoplastic materials from the dental appliance.

42. A method as recited in claim 41, wherein the step of trimming the excess material is accomplished by turning the dental appliance inside-out.

43. A method as recited in claim 41, wherein the step of trimming the excess material is accomplished by cutting into the embrasures between the teeth represented on the model.

44. A method as recited in claim 33, further comprising the steps of:
   a. separating the dental appliance from the model; and,
   b. heating the edges of the appliance with a flame torch to smooth the edges.

45. A method for readapting a dental appliance to closely conform to the contours and embrasures of a model representative of a patient's teeth, the method comprising the steps of:
   a. adapting the dental appliance from a thermoplastic sheet that has been heated at a first position close to a heating element of the vacuum forming device;
   b. removing the dental appliance from the model;
   c. trimming the excess material of the thermoplastic sheet from the dental appliance;
   d. placing the dental appliance on the model;
   e. attaching a retaining screen to a clamping frame of the vacuum forming table;
   f. placing the model and dental appliance on the screen,
   g. heating the dental appliance to a predetermined state of plasticity at a second position, the second position being located further away from the heating element than the first position;
   h. relocating the clamping frame from the second position to a third position resting on a surface of a vacuum forming table in order to place the model and dental appliance in close contact with negative pressure generated by a vacuum pump linked in negative pressure communication with the surface of the vacuum forming table;
   i. positioning an elastic membrane over the model and dental appliance, with the edges of the elastic membrane sealed to the surface of the vacuum forming table in order to sustain a negative pressure around model and the dental appliance;
   j. enabling the vacuum pump and allowing the vacuum pump to operate for a period of time until the dental appliance cools and conforms closely to the model; and
   k. removing the dental appliance from the model.

* * * * *

UNITED STATES PATENT AND TRADEMARK OFFICE
CERTIFICATE OF CORRECTION

PATENT NO. : 5,667,386
DATED : September 16, 1997
INVENTOR(S) : Dan E. Fischer

Figure 1:
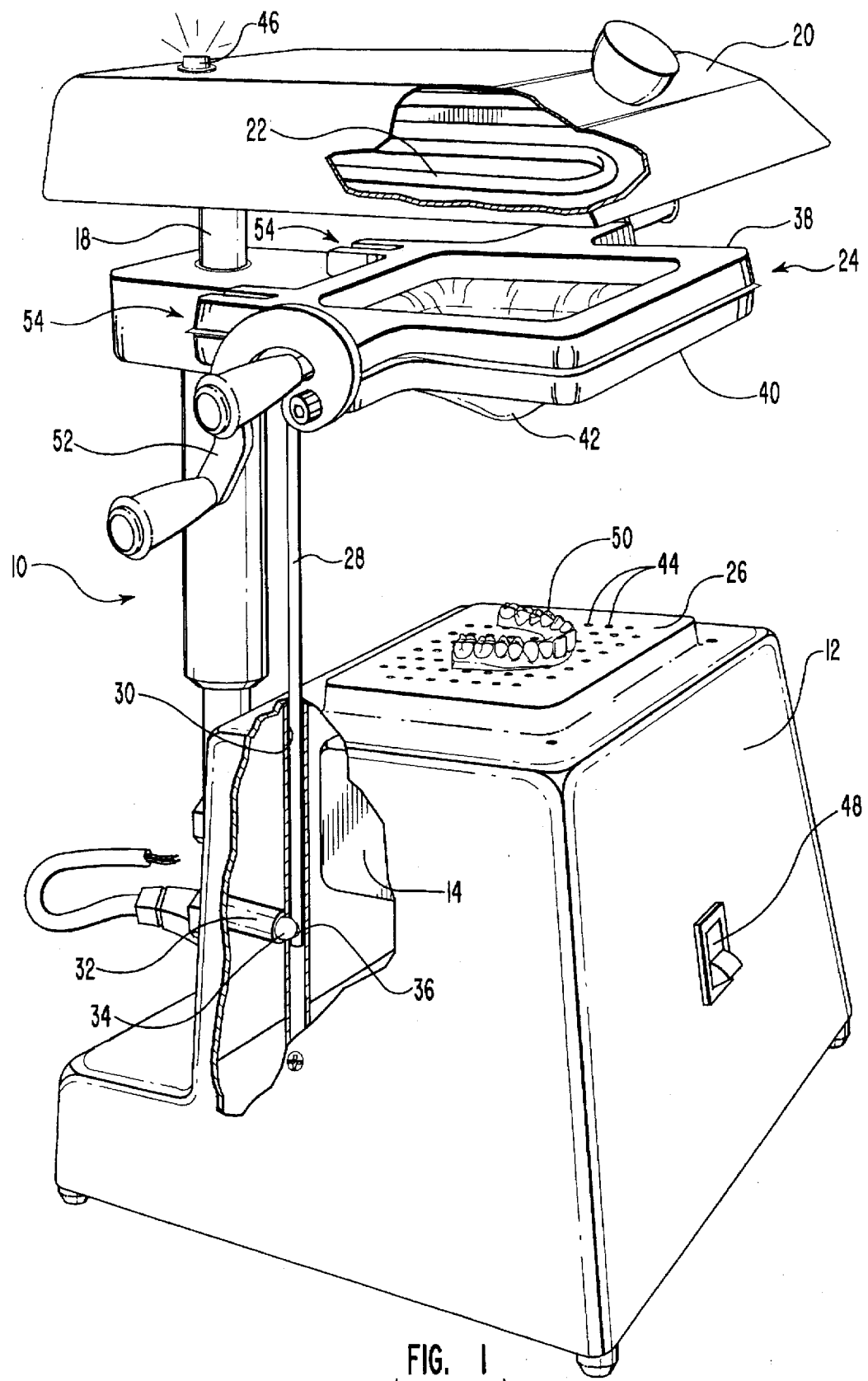
FIG. 1 is a perspective view of a vacuum forming device currently used in the art. The clamping frame of the vacuum forming device is shown at an elevated position close to the heating element, and a thermoplastic sheet is retained within the clamping frame, while a model is shown located on the vacuum forming table. A first cutaway section shows the heating element, and a second cutaway section shows the vacuum pump and the guide rod with the spring-loaded ball and corresponding indentation in the guide rod.

It is certified that error appears in the above-identified patent and that said Letters Patent is hereby corrected as shown below:

Figure 1, change reference numeral "54" to --55-- (as shown on the attached page)

Figure 2:
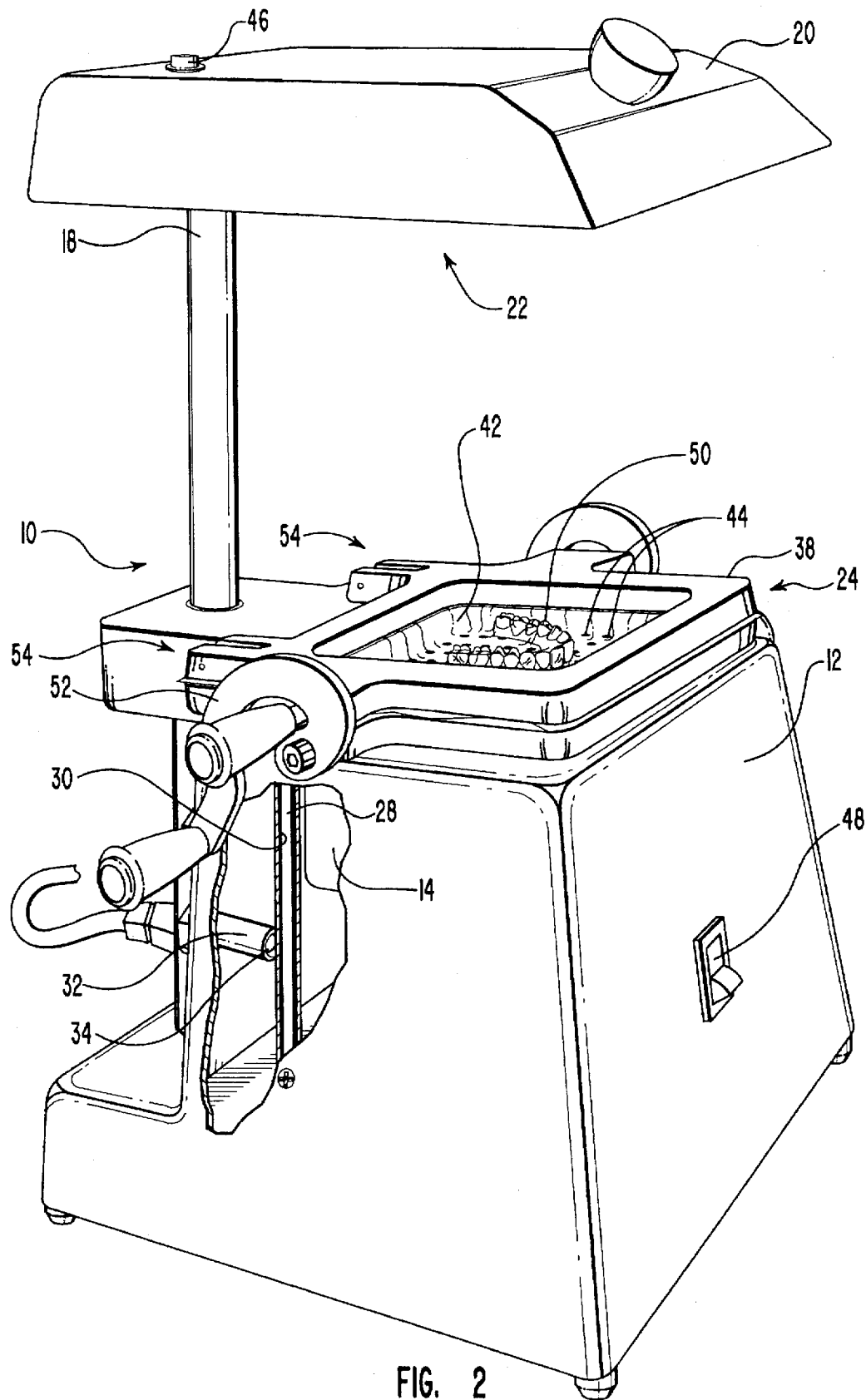
FIG. 2 is a perspective view of the vacuum forming device of the prior art, showing the clamping frame resting on the vacuum forming table with the thermoplastic sheet positioned over the model and the vacuum pump enabled. A cutaway view shows the vacuum pump, guide rod, and spring-loaded ball.

Figure 2, change reference numeral "54" to --55-- (as shown on the attached page)

Col. 2, line 6, change "hinges 54" to --hinges 55--

Col. 2, line 46, change "vacuum pump 24" to --vacuum pump 14--

Col. 7, line 29, change "flame" to --frame--

Col. 9, line 22, change "flame" to --frame--

Col. 13, line 27, change "liar" to --for--

Col. 16, line 27, change "damp" to --clamp--

Col. 16, line 49, change "three" to --force--

Signed and Sealed this

Ninth Day of June, 1998

Attest:

BRUCE LEHMAN

Attesting Officer

Commissioner of Patents and Trademarks